United States Patent [19]

Laidler et al.

[11] 4,383,112
[45] May 10, 1983

[54] CHIRAL AMINO-ALCOHOL COMPLEXES

[75] Inventors: Dale A. Laidler, Huntington; David J. Milner, Manchester, both of England

[73] Assignee: Imperial Chemical Industries Limited, London, England

[21] Appl. No.: 167,158

[22] Filed: Jul. 8, 1980

[30] Foreign Application Priority Data

Jul. 13, 1979 [GB] United Kingdom ............... 7924519

[51] Int. Cl.³ .................. C07D 213/00; C07D 215/00
[52] U.S. Cl. ................................. 542/414; 548/541; 548/203; 548/532; 548/235; 548/342; 548/533; 548/343; 548/556; 548/534; 548/536; 548/557; 548/558; 548/559; 548/531; 548/402; 548/404; 548/561; 548/542; 548/530; 548/505; 548/516; 548/503; 542/420; 542/422; 542/424; 546/2; 546/6; 546/176; 546/268; 546/283; 546/329; 546/334; 548/544; 548/546; 548/550; 548/537; 548/539; 548/540
[58] Field of Search ............... 546/329, 283, 176, 268, 546/334, 2, 6; 260/326.5 A, 326.15, 326.5 B, 326.52; 542/414, 420, 422, 424; 548/203, 235, 342, 343, 335, 336

[56] References Cited

U.S. PATENT DOCUMENTS

| | | | |
|---|---|---|---|
| 3,868,401 | 2/1975 | Aratani et al. | 260/468 H |
| 4,029,683 | 6/1977 | Aratani et al. | 260/438.1 |
| 4,029,690 | 6/1977 | Aratani et al. | 260/468 H |
| 4,119,652 | 10/1978 | Knowles et al. | 546/2 |
| 4,124,533 | 11/1978 | Knowles et al. | 546/2 |

FOREIGN PATENT DOCUMENTS

| | | |
|---|---|---|
| 50-160241 | 12/1975 | Japan . |
| 1455189 | 11/1976 | United Kingdom . |
| 1459285 | 12/1976 | United Kingdom . |
| 1499094 | 1/1978 | United Kingdom . |

OTHER PUBLICATIONS

Adam et al., J. Chem. Soc., 1979, pp. 234-235.
Harai et al., Agric Biol. Chem. 40 (1976), pp. 169-174.
Aratani et al., Tet. Letters, 1975, pp. 1707-1710.
Aratani et al., Tet. Letters, 1977, pp. 2599-2602.
Orioli et al., J. Am. Chem. Soc., 88, (1966), pp. 277-280.
MacDonald et al., Inorg. Chim. Acta., 33, (1979), p. L183.
Nakamura et al., J. Am. Chem. Soc., 100 (1978), pp. 3443-3448.
Nakamura et al., J. Am. Chem. Soc., 100 (1978), pp. 6544-6546.
Sacconi et al., J. Chem. Soc., 1964, pp. 276-280.
Nozaki et al., Tetrahedron 24 (1968), pp. 3655-3669.
Zassinovich, J. Orgmet. Chem., 133 (1977), pp. 377-384.
Robinson et al., Inorg. Chem., 2 (1963), pp. 1178-1181.
Hubert, Synthesis, 9 (1976), pp. 600-602.
Aratani, Shokubai 19 (1977), pp. 327-333.

*Primary Examiner*—Arthur P. Demers
*Attorney, Agent, or Firm*—Cushman, Darby & Cushman

[57] ABSTRACT

Chiral Schiff bases according to the general formula:

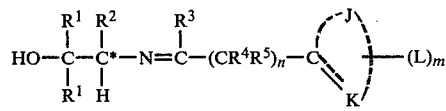

and transition metal complexes thereof, wherein $C^*$ is an asymmetric carbon atom, $R^1$ and $R^2$, which may be the same or different are alkyl, aralkyl, aryl or alkaryl, $R^3$ is hydrogen, alkyl, aralkyl, aryl or alkaryl, $R^4$ and $R^5$, which may be the same or different, are hydrogen or lower alkyl or, where n is 1, may with the cyclic ring to which $CR^4R^5$ is attached form a fused system, J is a chain of 3 or 4 atoms which may all be carbon atoms or may be a mixture of carbon atoms and one or more hetero atoms which may be the same or different, which chain with the group G----K forms an aromatic system, K is nitrogen,

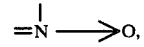

or —NH—, L, each of which may be the same or different, represents a substituent attached to a carbon atom in the chain J and is hydrogen, alkyl, aralkyl, alkaryl, aryl or a substituent containing a hetero-atom; or two L's together with the cyclic ring to which they are attached form a fused system, n is 0, 1 or 2, m is the number of carbon atoms in the chain J. The transition metal is for example copper (II), chromium (II), manganese (II), iron (II), cobalt (II) nickel (II) or palladium (II). The aforesaid complexes may be used as catalysts in the cyclopropanation of olefins by diazoacetates to form insecticide or insecticide precursors.

14 Claims, No Drawings

CHIRAL AMINO-ALCOHOL COMPLEXES

This invention relates to novel chiral Schiff bases, to novel chiral metal complexes, and to the preparation of such bases and complexes; such complexes may be used as catalysts in the preparation of cyclopropane carboxylic acid esters which are compounds useful as insecticides, or insecticide intermediates.

It will be appreciated by those skilled in the art that cyclopropane carboxylic acid esters may, where the cyclopropane ring is appropriately substituted, exist in various geometrical and stereoisomeric forms. In particular, the carbon atom bearing the carboxylic acid group may have the S or R configuration.

Moreover, it is known that, where insecticides are derived from cyclopropane carboxylic acids, the isomer having the 1R configuration is insecticidally more effective than its stereoisomer having the 1S configuration.

Cyclopropane carboxylic acid esters which are insecticides or insecticide precursors may be prepared by the reaction of an ester of diazoacetic acid with the carbon-carbon double bond of a suitable monoene or diene. It is known that where this reaction is catalysed by chiral copper complexes an enantiomeric excess of esters having a predetermined configuration may be obtained. United Kingdom Patent Specification No. 1455189 and Japanese Patent Kokai No. 160241/75 disclose the preparation of cyclopropane carboxylic acid esters useful as insecticide intermediates from dienes using copper complexes of Schiff bases as catalysts. The Schiff bases were derived from salicyclaldehydes, or derivatives thereof, and notional derivatives of aminoacids.

We have now found that the reaction of diazoacetic ester with a suitable monoene or diene may be catalysed by certain novel chiral metal complexes and that an enantiomeric excess of cyclopropane carboxylic acid esters having a predetermined configuration is often obtained. Moreover, where a monoene is used an excess of the cis isomer is often formed.

In the novel chiral metal complexes the metal is coordinated with a novel chiral Schiff base derived from a heterocyclic carbonyl compound and a chiral amine which chiral amine has (a) an asymmetirc carbon atom which bears the amino group and (b) a hydroxyl group on the carbon atom adjacent the aforesaid asymmetric carbon atom.

In one aspect therefore the present invention provides chiral Schiff bases according to the general formula:

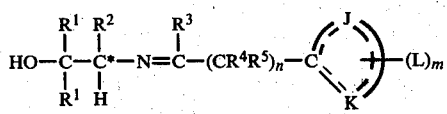

and transition metal complexes thereof, wherein

C* is an asymmetric carbon atom, $R^1$ and $R^2$, which may be the same or different are alkyl, aralkyl, aryl or alkaryl, $R^3$ is hydrogen, alkyl, aralkyl, aryl or alkaryl, $R^4$ and $R^5$, which may be the same or different, are hydrogen or lower alkyl or, where n is 1, may with the cyclic ring to which $CR^4R^5$ is attached form a fused system, J is a chain of 3 or 4 atoms which may all be carbon atoms or may be a mixture of carbon atoms and one or more hetero atoms which may be the same or different, which chain with the group C===K forms an aromatic system, K is nitrogen,

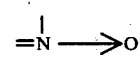

or —NH—,

L, each of which may be the same or different, represents a substituent attached to a carbon atom in the chain J and is hydrogen, alkyl, aralkyl, alkaryl, aryl or a substituent containing a heteroatom; or two L's together with the cyclic ring to which they are attached form a fused system, n is 0, 1 or 2, m is the number of carbon atoms in the chain J.

By lower alkyl group we mean an alkyl group having up to five carbon atoms, e.g. methyl, ethyl, n-propyl and n-butyl.

By aromatic system we mean a substantially planar cyclic conjugated system containing $(4z+2)\pi$ electrons, where z is a positive integer.

Specific examples of the conjugated chain J are —C=C—C=C—, —C=N—C=C—, —C=C—N=C—, —N=C—C=C—, —S—C=C—, —O—C=C— —NH—C=C—, =C—C=C— and =C—N=C—.

Examples of substituents $R^1$ and $R^2$ in general formula I are methyl, ethyl, propyl, iso-propyl, butyl, iso-butyl, sec-butyl, t-butyl, octyl, cyclohexyl, cyclohexylmethyl, benzyl, benzhydryl, 2,2-diphenyl-ethyl, phenyl, tolyl and naphthyl.

Examples of alkyl groups represented by L and $R^3$ are methyl, ethyl, n-propyl, iso-propyl, n-butyl, iso-butyl, sec-butyl, tert-butyl, n-pentyl, n-hexyl, cyclohexyl, n-octyl 2-ethylhexyl, n-decyl and n-dodecyl.

Examples of aralkyl groups represented by $R^3$ are benzyl and 2-phenylethyl.

Where L contains one or more heteroatoms specific examples include OH, $OR^6$, $OCOR^6$, CHO, $COR^6$, $CO_2H$, $CO_2R^6$, CN, $CONH_2$, $NH_2$, $NHR^6$, $NR_2^6$, $NHCOR^6$, $NO_2$, SH, $SR^6$, $SOR^6$, $SO_3H$, $SO_3R^6$ or a halogen atom, where $R^6$ is alkyl, aralkyl or aryl.

Preferably $R^1$ is a substituted phenyl group, $R^3$ is hydrogen, n is 0 and the cyclic ring of general formula I is a pyridine nucleus, quinoline nucleus or a pyrrole nucleus. It is also preferred that $R^1$ represents a phenyl group having a substituent at the 2-position or having substituents at the 2,5-position or 2,6-positions and that $R^2$ is a phenyl group.

Examples of substituted phenyl groups are 2-methoxyphenyl, 2-ethoxyphenyl, 2-propoxyphenyl, 2-isopropoxyphenyl, 2-butoxyphenyl, , 2-t-butoxyphenyl, 2-octyloxyphenyl,, 2-benzyloxyphenyl, 2-phenoxyphenyl, 2-methoxy-5-methylphenyl, 2-butoxy-5-methylphenyl, 2-benzyloxy-5-t-butylphenyl, 4-methoxybiphenyl-3-yl, 2,5-dimethoxyphenyl, 2,5-dibutoxyphenyl, 2,5-dioctyloxyphenyl and 2,5-dibenzyloxyphenyl.

Examples of specific heterocyclic carbonyl compounds from which novel chiral Schiff bases according to the present invention may be prepared include inter alia 2-pyridinecarboxaldehyde, 2-pyridinecarboxaldehyde-N-oxide, 8-quinoline carboxaldehyde, pyridoxal, and 2-pyrrolecarboxaldehyde.

Where it is desired to form a novel chiral Schiff base of the present invention from an enantiomer of a chiral amine preferably having a hydroxyl group on the carbon atom adjacent the carbon atom bearing the amino group the aforesaid enantiomer may be obtained by, for example, optical resolution of a mixture of the appropriate enantiomers. Preferably, however, the aforesaid enantiomer is prepared from an enantiomer of a chiral starting material. Naturally occurring α-amino acid esters are convenient starting materials and they may be converted into suitable chiral amines by the known reaction with appropriate Grignard reagents. An example of a suitable chiral amine derived from an amino acid is 2-amino-1,1-di-(2-methoxyphenyl)-3-phenylpropan-1-ol.

The compounds of formula I having an oxygen atom on the ring nitrogen (i.e. K is N→O) may be obtained by oxidation of the corresponding compounds of formula I in which the ring nitrogen is unsubstituted. A suitable oxidising agent for this purpose is hydrogen peroxide.

It is believed that the chiral metal complexes according to the present invention have structures represented by formulae II, III and IV

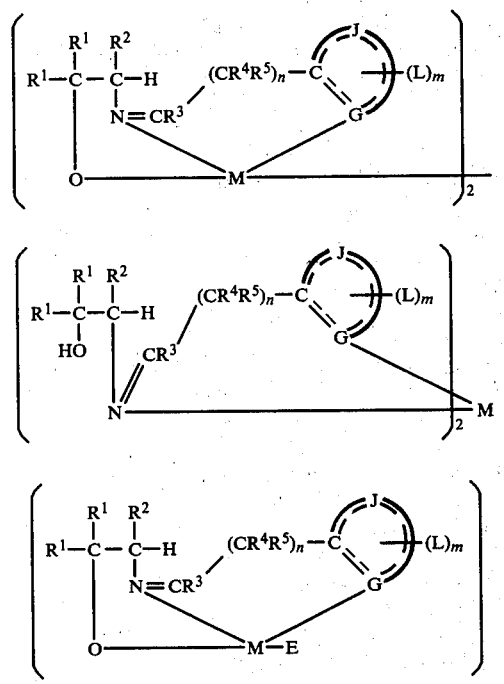

wherein $R^1$, $R^2$, $R^3$, $R^4$, $R^5$, J, L, m and n have the meanings previously ascribed to them, E is a monodenate neutral ligand, M is a metal from the first or second series of the main group of transition metals, and G is =N—, =N→O or —N—.

By transition metal we mean a metal which, in any one of its commonly occurring oxidation states, has a partly filled d shell only. In the first series the partly filled d shell is 3d and in the second series the partly filled d shell is 4d.

Preferably the metal is copper (II), chromium (II), manganese (II), iron (II), cobalt (II), nickel (II) or palladium (II). Particularly preferably the metal is copper (II).

Examples of ligand E in general formula IV include Lewis bases such as amines, e.g. pyridine, and tertiary phosphine oxides.

It will be appreciated that complexes according to the general formula II are binuclear and that in complexes according to the general formulae II and IV the Schiff base behaves as a tridentate ligand and that in complexes according to the general formula III the Schiff base behaves as a bidentate ligand.

A preferred group of metal complexes within the invention are those according to general formula III since they often give a higher optical yield than that given by the metal complexes according to the general formulae II or IV.

It will be appreciated that in chiral metal complexes according to the present invention where G is =N— or =N→O the metal carries a positive charge and an anion is necessary to provide an electrically neutral complex. The anions associated with the metal complexes may be inorganic or organic, provided that they are derived from strong acids having a pKa value less than 2.5.

The anions should not be oxidising or reducing agents or otherwise chemically reactive with diazo compounds or other materials used in the preparation of the cyclopropane derivatives. Suitable anions include inter alia halide, fluoroborate, methyl sulphate, bisulphate, aromatic sulphonates, fluorosilicate, sulphate, tetrafluoroborate and tetraphenyl-borate.

The novel chiral Schiff bases according to the present invention are conveniently prepared by reacting a chiral primary amine with a heterocyclic carbonyl compound. Preferably the carbon atom adjacent the carbon atom bearing the amino group bears a hydroxyl or protected hydroxyl group, more preferably a hydroxyl group. The reaction is preferably carried out in the presence of an inert solvent in which the Schiff base in insoluble and is effected near the reflux temperature of the solvent.

Suitable solvents include aromatic hydrocarbons e.g. toluene, alcohols, e.g. methanol, and chlorinated hydrocarbons.

Various methods are available for preparing novel transition metal complexes of chiral Schiff bases according to the present invention. For example, a novel chiral Schiff base may be treated with a transition metal inorganic salt, e.g. copper (II) chloride, to form the corresponding complex, and then, where it is derived to form a fluoroborate, with a suitable fluoroborate, typically in excess, e.g. sodium fluoroborate, to form the corresponding fluoroborate complex (hereinafter Method A). A solution of a suitable chiral primary amine may be mixed, e.g. by dropwise addition, to a suspension of a suitable transition metal complex, e.g. bis(2-pyrrolealdehydato) copper (II), the reaction mixture stirred, for example for 1 hour, and a novel chiral complex according to the present invention isolated (hereinafter Method B). A solution of a chiral Schiff base according to the present invention, preferably in a suitable solvent, e.g. warm methanol, may be added to a suspension of a suitable transition metal complex, e.g. bis(salicylaldehydato) copper (II), in a suitable solvent, e.g. methanol, and the resulting mixture stirred to form a novel chiral complex according to the present invention (hereinafter Method C). A chiral Schiff base according to the present invention and a transition metal carboxylate, e.g. copper (II) acetate, preferably dissolved in a suitable solvent, e.g. ethanol, may be heated, preferably under reflux where a suitable solvent is used, for an appropriate time, e.g. 10 minutes; removal of the solvent, where it is used, leaves a binuclear transition metal complex according to the present invention (hereinafter Method D).

Accordingly a further aspect of the present invention provides a method for the preparation of novel chiral metal complexes which method comprises
(a) reacting a novel chiral Schiff base according to a first aspect of the present invention with a transition metal inorganic salt to form the corresponding transition metal complex and then optionally with a suitable fluoroborate to form the corresponding transition metal fluoroborate complex or,
(b) reacting a suitable chiral primary amine compound with a suitable transition metal complex or,
(c) reacting a novel chiral Schiff base according to a first aspect of the present invention with a suitable transition metal complex or,
(d) reacting a novel chiral Schiff base according to a first aspect of the present invention with a transition metal carboxylate.

The chiral metal complexes according to the invention may be employed as catalysts in the preparation of cyclopropane carboxylic acid esters of general formula:

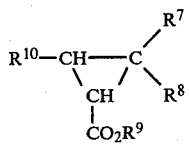   V by reacting a compound having the general formula:

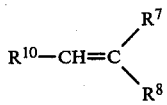   VI with an ester of, for example, diazoacetic acid.

In the formulae V and VI above:
$R^7$ represents a hydrogen atom or a lower alkyl group,
$R^8$ represents a lower alkyl group,
$R^9$ represents a lower alkyl group, or a group which forms insecticidally active esters with chrysanthemic acid, e.g. 3-phenoxybenzyl or α-substituted 3-phenoxybenzyl and
$R^{10}$ represents:

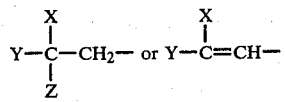

in which Z represents fluorine, chlorine or bromine, X and Y, which may be the same or different, represent fluorine, chlorine, bromine, lower alkyl group, $Q(CF_2)_q$— (in which Q is hydrogen, fluorine or chlorine and q is 1 or 2) or

where each of U, V, W, independently represents an atom of hydrogen, fluorine or chlorine except that where one of X and Y represents a group of formula $Q(CF_2)_2$— where Q is as defined above, the other of X and Y represents an atom of fluorine, chlorine or bromine or a group of formula:

where U, V and W are as defined hereinbefore.

Although the chiral metal complexes according to the present invention may be used for the preparation of many of the compounds of formula V they are particularly useful for the preparation of compounds wherein $R^7$ and $R^8$ are methyl, $R^9$ is ethyl, 3-phenoxybenzyl, α-cyano-3-phenoxybenzyl or α-ethynyl-3-phenoxybenzyl, and $R^{10}$ is $Cl_2C=CH-$, $CF_3CCl=CH-$, $CF_3CCl_2CH_2-$, $Cl_3C-CH_2-$, or $(CH_3)_2C=CH-$.

The use of the novel chiral complexes of the present invention as catalysts in the reaction of monoenes, or suitable dienes, with a diazoacetate ester to form insecticides or insecticide intermediates is more fully described in our copending United Kingdom Patent application Nos. 7924521 and 7924522 respectively.

Compounds of general formula V wherein $R^7$ and $R^8$ represent methyl, $R^9$ represents 3-phenoxybenzyl or α-cyano-3-phenoxybenzyl and $R^{10}$ represents $Cl_2C=CH-$ are known to be potent insecticides when they have the 1R configuration; the isomers having the so-called 1R cis configuration being particularly potent and having more insecticidal activity than the isomers having the 1R trans configuration. The isomers having the 1S configuration have less insecticidal activity. By cis we mean that the hydrogens at C1 and C3 of the cyclopropane ring are in the cis relationship to one another and by trans we mean that the hydrogens at C1 and C3 of the cyclopropane ring are in the trans relationship to one another.

The reaction of a compound of general formula VI with a diazoacetate is preferably carried out in the presence of an inert solvent in which the cyclopropane product of formula V is soluble.

Conveniently the solvent used is immiscible with water to facilitate preparation of the diazoacetic ester. More preferably the solvent also has a boiling point lower than that of the monoene or diene of formula VI to facilitate recovery of unreacted monoene or diene.

Suitable solvents include saturated chlorinated hydrocarbon solvents, such as ethylene dichloride, dichloromethane, tetrachloroethane, carbon tetrachloride and the like.

A wide variety of metal complexes according to the present invention may be used as catalysts, the precise 1R:1S ratio of the product being dependent inter alia upon the actual complex used.

The concentration of catalyst in the reaction mixture is not critical, but generally concentrations in the range 0.00001 to 1 g atoms of transition metal per liter of reaction mixture, and especially 0.005 to 1 g atoms, are suitable.

The temperature of reaction is generally in the range 0° to 130° C. preferably 10° C. to 90° C.

The diazoacetic acid ester may be prepared by reacting a water soluble acid addition salt (e.g. the hydrochloride) of an ester of glycine with an alkali metal nitrite in an aqueous medium, which is stirred with a water-immiscible solvent into which the diazoacetic acid ester is extracted. Alkali metal nitrites which may be used, are for example, the potassium or sodium salts, and the reaction with the glycine ester is preferably carried out in the presence of an acid catalyst, for example, sulphuric acid.

The solution of diazoacetic acid ester thus formed is then added to a solution of the monoene or diene of formula VI maintained at the desired temperature, and containing the catalyst, usually in solution.

The ratio of monoene or diene to diazoacetic ester employed in the processes herein disclosed is normally in the range 1:10 to 10:1. It is usual to use enough monoene or diene to react with all the diazoacetate. However, where high conversion of monoene or diene to cyclopropane derivative are desired an excess of diazoacetate may be employed.

Progress of the reaction may be monitored by measuring nitrogen evolution, which may also be used to determine yield of total products, the proportion of the desired product being readily determined by gas liquid chromatography (g.l.c.)

Separation of the desired product from the reaction mixture may be achieved by any convenient means but it is generally convenient to first distil off the solvent, the monoene or diene, then any esters of maleic and fumaric acids and finally the required product. Alternatively, the crude product, where it is a lower alkyl ester, after removal of solvent and unreacted monoene or diene may be used as an intermediate without further purification.

The reaction may also be performed continuously by forming the diazoacetic ester in a first vessel and continuously transferring it, in a solvent, to a second vessel where it is reacted immediately with the monoene or diene, as described and claimed in our British Patent No. 1,459,285.

It may sometimes be difficult to predict which optical isomer of a particular amino-acid (from which the chiral metal complexes according to the present invention are notionally derived) will give an enhanced proportion of the desired optical isomer of the cyclopropane product; but this may be readily determined experimentally by testing each optical isomer in turn and determining the product distribution, e.g. by g.l.c. analysis.

We have found that where chiral metal complexes according to the present invention which are notionally derived from S-amino acids, which are often the naturally occurring isomer, are used to catalyse the reaction of a diazoacetate with a monoene an excess of cis cyclopropane isomers over trans isomers is often formed and in the cis pair of isomers the 1R enantiomer is formed in excess.

Generally, we have found surprisingly, in the light of the disclosure in United Kingdom Patent Specification No. 1,455,189, that where chiral transition metal complexes according to the present invention which are notionally derived from S-amino acids are used to catalyse the reaction of a diazoacetate with a halogenated diene there is within the pair of trans cyclopropane isomers formed in the reaction an excess of the 1R enantiomer.

Our process may be used to produce a variety of esters of a particular cyclopropane carboxylic acid, the particular ester produced being dependent upon the particular glycine ester used. Thus the process may be used to produce simple alkyl esters, which are useful as intermediates in the preparation of insecticides, or it may be used to produce the insecticides themselves. In the latter case the glycine ester must correspond to the required insecticidal ester. Examples of glycine esters of this type include the ester with 3-phenoxybenzyl alcohol, and with 5-benzyl-3-furyl methanol.

The invention will be illustrated by the following Examples.

EXAMPLE 1

This example illustrates the preparation of novel chiral Schiff bases.

(a) A mixture of S-2-amino-1,1-di(2-methoxyphenyl)-3-phenyl-1-propanol (7.21 g) (prepared by the method of A McKenzie, R. Roger and G. O. Wills, J. Chem. Soc., 1926, 779) and freshly distilled 2-pyridine-carboxaldehyde (2.35 g) were heated at reflux in anhydrous toluene (50 ml) for 4 hours. The reaction mixture was cooled to room temperature, dried (MgSO$_4$) and evaporated in vacuo to leave a viscous brown syrup. On standing overnight in a dichloromethane/pet. ether (b.p. 40°–60° C.) mixture, the syrup yielded light brown cubic crystals which were filtered off, washed with cold pet. ether and dried (2.9 g). The mother liquors were concentrated and yielded two further crops of crystals. (Total yield 5.9 g, 65%). Recrystallisation of the crystals from methanol gave tan crystals m.p. 100°–105° C.

Elemental analysis for $C_{29}H_{28}N_2O_3$

|  | C | H | N |
|---|---|---|---|
| Found: | 75.01 | 5.38 | 5.87 |
| Calculated: | 76.97 | 6.27 | 6.19 |

(b) S-2-Amino-1,1-di(2-methoxyphenyl)-3-phenyl-1-propanol (1.45 g) and 8-quinolinecarboxaldehyde (0.625 g) were refluxed together in absolute alcohol (40 ml) for 3 hours Decolourising charcoal was added to the dark solution and refluxing was continued for a further 1 h. After filtration the solution was concentrated in vacuo and a foam was obtained. This foam was dissolved in a small volume of dichloromethane and the product was precipitated as a light tan-coloured solid when an excess of ether was added. (1.12 g, 56%) m.p. 60°–63° C.

Elemental analysis for $C_{33}H_{30}N_2O_3$

|  | C | H |
|---|---|---|
| Found: | 79.18 | 6.63 |
| Calculated: | 78.86 | 6.02 |

(c) S-2-Amino-1,1-di(2-methoxyphenyl)-3-phenyl-1-propanol (3.63 g) and 2-pyrrolecarboxaldehyde (0.95 g) were refluxed together in anhydrous toluene (40 ml) in an apparatus which included a Soxhlet extractor filled with molecular sieves (Type 4A). After 4 h the solvent was evaporated in vacuo and the residue was crystallised from ether-n-hexane to give the imine in two crops (total yield 3,85 g, 87%) m.p. 70°–72° C.

Elemental analysis for $C_{28}H_{28}N_2O_3$

|  | C | H | N |
|---|---|---|---|
| Found: | 75.70 | 6.20 | 5.58 |
| Calculated: | 76.34 | 6.41 | 6.36 |

EXAMPLE 2

This example illustrates the preparation of novel chiral transition metal complexes.

A portion of the chiral Schiff base (0.828 g) prepared as in Example 1a, was dissolved in warm absolute alcohol (30 ml) and a solution of cupric chloride dihydrate (0.156 g) in distilled water (5 ml) was added dropwise over 30 minutes. The solution was stirred at room temperature for 30 minutes and then divided into two.

One half of the solution was evaporated to small bulk and the resulting solid was filtered off, washed with distilled water and dried in vacuo to afford the chloride of the mononuclear copper (II) complex of the Schiff base derived from 2-pyridine-carboxaldehyde and S-2-amino-1,1-di(2-methoxyphenyl)-3-phenyl-1-propanol which when recrystallised from dichloromethane/hexane melted at 170° C. with decomposition.

Elemental analysis for $C_{58}H_{56}O_6N_4CuCl_2$

|  | C | H | N | Cl | Cu |
|---|---|---|---|---|---|
| Found: | 64.73 | 5.95 | 5.30 | 8.65 | 7.80 |
| Calculated: | 67.01 | 5.43 | 5.39 | 6.82 | 6.11 |

A solution of sodium fluoroborate (0.100 g) in distilled water (5 ml) was added to the other half of the solution. The mixture was evaporated to small bulk and the resulting solid was filtered off, washed with distilled water and dried in vacuo to afford the fluoroborate of the mononuclear copper (II) complex of the Schiff base derived from 2-pyridinecarboxaldehyde and S-2-amino-1,1- di(2-methoxyphenyl)-3-phenyl-1-propanol m.p. 144°-146° C. (decomposition).

Elemental analysis for $C_{58}H_{56}O_6CuB_2F_8$

|  | C | H | N | Cu |
|---|---|---|---|---|
| Found: | 59.52 | 4.28 | 4.61 | 5.7 |
| Calculated: | 60.98 | 4.94 | 4.91 | 5.6 |

EXAMPLE 3

This example illustrates the preparation of a novel chiral transition metal complex.

The procedure of Example 2 was repeated except that the chiral Schiff base (0.290 g) derived from 8-quinoline-carboxaldehyde and S-2-amino-1,1-di(2-methoxyphenyl)-3-phenyl-1-propanol was used instead of the chiral Schiff base derived from 2-pyridine-carboxaldehyde and S-2-amino-1,1-di(2-methoxyphenyl)-3-phenyl-1-propanol. The novel chiral transition metal chloride complex was obtained as a pale green solid, m.p. 177°-180° C. (decomposition).

EXAMPLE 4

This example illustrates the preparation of a novel chiral transition metal complex.

The procedure of Example 2 was repeated except that the chiral Schiff Base (0.804 g) derived from 2-pyrrolecarboxaldehyde and S-2-amino-1,1-di(2-methoxyphenyl)-3-phenyl-1-propanol was used instead of the chiral Schiff base derived from 2-pyridine-carboxaldehyde and S-2-amino-1,1-di(2-methoxyphenyl)-3-phenyl-1-propanol. The novel chiral transition metal chloride complex was obtained as a blue-gray solid, m.p. 200°-205° C. (decomposition).

Elemental analysis for $C_{56}H_{54}N_4O_6Cu$

|  | C | H | N | Cu |
|---|---|---|---|---|
| Found: | 70.68 | 5.46 | 5.17 | 6.3 |
| Calculated: | 71.35 | 5.78 | 5.95 | 6.7 |

EXAMPLES 5-8

These examples illustrate the use of novel metal complexes as catalysts in the reaction of a diazoacetic ester with a halogenated diene of general formula VI.

1,1-Dichloro-4-methyl-1,3-pentadiene (DCMP-1,3) was added to the mononuclear copper (II) complexes of Schiff bases derived from heterocyclic carbonyl compounds and S-2-amino-1,1-di(2-methoxyphenyl)-3-phenyl-1-propanol under an atmosphere of nitrogen. A solution (0.25 ml) containing dodecane (1.76 m mole per ml) in a chlorinated solvent (1,2 dichloroethane or 1,1,2,2-tetrachloroethane) was added as a glc internal standard. The mixture was then heated to reaction temperature with stirring under an atmosphere of nitrogen. A solution containing DCMP-1,3 (60 m mole) and diazoacetic acid ethyl ester (DAE) in toluene (2 ml) was then added to the stirred mixture over a period of 20 hours. Nitrogen evolution was monitored throughout the reaction and small samples of the reaction mixture were withdrawn from time to time for glc analysis.

% yields were determined in terms of moles of ethyl 2,2-dimethyl-3(2,2-dichlorovinyl)cyclopropane carboxylate (PAE) per mole of nitrogen evolved (i.e. per mole of diazoacetic ester decomposd).

The solvent for the reaction (1,2-dichloroethane/toluene) was removed using a rotary evaporator and the PAE isolated by column chromatography using an alumina (type H) column. Unreacted DCMP-1,3 was washed from the column by elution with petroleum ether (40°-60° C.) and the PAE subsequently recovered by elution with diethyl ether. Diethyl fumarate and diethyl maleate co-products remained on the column.

The PAE was hydrolysed with ethanolic NaOH to give the free acid which was treated with thionyl chloride to give the acid chloride. This was reacted with 2-d-octanol to give a mixture of four isomers. These were analysed by glc on a 15 ft column of 5% LAC-2R-446 on Embacel at 125° C. The results are given in Table 1 from which it can be seen that for the cis pair of isomers an enantiomeric excess of the 1S enantiomer is obtained when the reaction of 1,1-dichloro-4-methyl-1,3-pentadiene with diazoacetic acid ethyl ester is catalysed by a mononuclear copper complex of a Schiff base notionally derived from an S-amino-acid. It is expected that employing in this reaction the metal complex at least notionally derived from the enantiomeric R-amino acid would produce an enantiomeric excess of the 1R enantiomer in the cis pair of isomers of ethyl 3-(2,2-dichlorovinyl)-2-,2-dimethyl cyclopropane carboxylate, the precursors of the insectidially more active isomers.

TABLE 1

Reactions of 1,1-dichloro-4-methyl-1,3-pentadiene with ethyl diazoacetate (DAE) using as catalysts copper (II) complexes of Schiff bases derived from S-2-amino-1,1-di(2-methoxyphenyl)-3-phenyl-1-propanol and heterocyclic carbonyl compounds.

| Example No. | Heterocyclic carbonyl compound | Catalyst conc. (m.moles) | Olefin conc. (m.moles) | DAE conc. (m.moles) | Solvent | Temp (°C.) | Yield of cyclopropane derivative (%) a | cis: trans | cis-1R,3S | cis-1S,3R | trans-1R,3R | trans-1S,3R |
|---|---|---|---|---|---|---|---|---|---|---|---|---|
| c | (Cu bronze) | 4.7 | 14.6 | 4.0 | DCE | 96 | 45 | 43:57 | 21.5 | 21.5 | 28.5 | 28.5 |
| c | (Raney Cu) | 0.6 | 40 | 8.0 | PhMe | 75 | 26 | 44:56 | 22 | 22 | 28 | 28 |
| c | d | 0.4 | 120 | 15 | PhMe | 50 | 33 | 40:60 | 17 | 23 | 23.5 | 36.5 |
| 5 | e | 0.1 | 40 | 8.0 | DCE | 75 | 3 | 41:59 | 17 | 24 | 32 | 29 |
| 6 | f | 0.1 | 40 | 8.0 | DCE | 75 | 15 | 42:58 | 15 | 27 | 32 | 26 |
| 7 | g | 0.1 | 40 | 8.0 | PhMe/DCE | 70 | 16 | 43:57 | 21 | 22 | 33 | 24 |
| 8 | h | 0.05 | 60 | 15 | DCE | 50 | — | 50:50 | 23.5 | 26.5 | 21.7 | 28.3 | a Yield based on percentage decomposition of ethyl diazoacetate
c Comparative example
d Salicylaldehyde
e 2-Pyridinecarboxaldehyde:chloride
f 8-Quinolinecarboxaldehyde:fluoroborate
g 2-Pyrrolecarboxaldehyde
h 2-Pyridinecarboxaldehyde:fluoroborate

EXAMPLES 9–14

These examples illustrate the use of the novel metal complexes as catalysts in the reaction of a diazoacetic ether with a halogenated monoene of general formula VI.

2,2-dichloro-5-methyl-1,1,1-trifluorohex-4-ene and a measured quantity of the appropriate catalyst as a mononuclear copper (II) complex of the Schiff base derived from a heterocyclic carbonyl compound and S-2-amino-1,1-di(2-methoxyphenyl)-3-phenyl-1-propanol were stirred at reaction temperature under an atmosphere of nitrogen. A burette was charged with a solution comprising the olefin, ethyl diazoacetate and toluene. This solution was added to the suspension of catalyst in olefin at a constant rate of approximately 1.3 ml per hour, and the nitrogen evolved during the reaction was collected. After 20 hours at reaction temperatures the addition of the diazoacetate and olefin solution was complete and the volume of nitrogen collected was measured (approximately 100% of theoretical nitrogen evolved for total decomposition of the ethyl diazoacetate). The reaction mixture was worked up and the isomer ratio determined as in Examples 5–8. The results are shown in Table 2 from which it can be seen that an excess of the cis isomer is formed and that in the pair of cis enantiomers an enantiomeric excess of the 1R cis enantiomer is obtained when the reaction of 2,2-dichloro-5-methyl-1,1,1-trifluorohex-4-ene with diazoacetate acid ethyl ester is catalysed by a mononuclear copper (II) complex of a Schiff base notionally derived from an S-amino acid.

EXAMPLES 15 and 16

This example illustrates the use of the novel metal complexes of the present invention as catalysts in the reaction of a diazoacetic ester with a halogenated monoene of general formula VI.

The general procedure of Examples 9 to 12 was repeated except that 1,1,1-trichloro-4-methyl-3-pentene was used instead of 2,2-dichloro-5-methyl-1,1,1-trifluorohex-4-ene.

The results are shown in Table 3 from which it can be seen that an excess of cis isomers are formed.

TABLE 2

Reactions of 2,2-dichloro-5-methyl-1,1,1-trifluorohex-4-ene with ethyl diazoacetate (DAE) using as catalysts copper (II) complexes of Schiff bases derived from S-2-amino-1,1-di(2-methoxyphenyl)-3-phenyl-1-propanol and heterocyclic carbonyl compounds

| Example No. | Heterocyclic carbonyl compound | Catalyst conc. (m.moles) | Olefin conc. (m.moles) | DAE conc. (m.moles) | Solvent | Temp (°C.) | Yield of cyclopropane derivative (%) a | cis: trans | cis-1R,3S | cis-1S,3R | trans-1R,3R | trans-1S,3R |
|---|---|---|---|---|---|---|---|---|---|---|---|---|
| c | (Raney Cu) | 0.6 | 18.1 | 3.5 | PhMe | 75 | 27 | 55:44 | 27.5 | 27.5 | 22 | 22 |
| c | d | 0.05 | 11.3 | 2.0 | PhMe/DCE | 65 | 12 | 62:38 | 39 | 23 | 24 | 14 |
| 9 | e | 0.1 | 22.6 | 7.5 | PhMe/DCE | 70 | 17 | 69:31 | 43 | 26 | 13 | 19 |
| 10 | f | 0.1 | 22.6 | 7.5 | PhMe/DCE | 70 | 12.5 | 63:37 | 40 | 23 | 12 | 25 |
| 11 | g | 0.05 | 18.1 | 3.5 | PhMe/DCE | 70 | — | 58:42 | 35 | 23 | 18 | 24 |
| 12 | h | 0.05 | 25 | 5.0 | PhMe | 70 | 14 | 54:46 | 29 | 25 | 20 | 26 |
| 13 | e | 0.2 | 22.6 | 7.5 | PhMe/DCE | 50 | 9.4 | 60:40 | 36 | 24 | 17 | 23 |
| 14 | i | 0.2 | 22.6 | 7.5 | PhMe/ | 50 | 7.0 | 69:31 | 43 | 26 | 12 | 19 |

TABLE 2-continued

Reactions of 2,2-dichloro-5-methyl-1,1,1-trifluorohex-4-ene with ethyl diazoacetate (DAE) using as catalysts copper (II) complexes of Schiff bases derived from S-2-amino-1,1-di(2-methoxyphenyl)-3-phenyl-1-propanol and heterocyclic carbonyl compounds

| Example No. | Heterocyclic carbonyl compound | Catalyst conc. (m.moles) | Olefin conc. (m.moles) | DAE conc. (m.moles) | Solvent | Temp (°C.) | Yield of cyclopropane derivative (%) a | Isomer distribution (%) | | | | |
|---|---|---|---|---|---|---|---|---|---|---|---|---|
| | | | | | | | | cis: trans | cis-1R,3S | cis-1S,3R | trans-1R,3R | trans-1S,3R |
| | | | | | DCE | | | | | | | | a Yield based on percentage decomposition of ethyl diazoacetate
c Comparative experiment
d Salicylaldehyde
e 2-Pyridinecarboxaldehyde:chloride
f 2-Pyridinecarboxaldehyde:fluoroborate
g 8-Quinolinecarboxaldehyde:fluoroborate
h 2-Pyrrolecarboxaldehyde
i 2-Pyrridinecarboxaldehyde:chloride

TABLE 3

Reactions of 1,1,1-trichloro-4-methyl-3-pentene with ethyl diazoacetate (DAE) using as catalysts copper (II) of Schiff bases derived from S-2-amino-1,1-di(2-methoxylphenyl)-3-phenyl-1-propanol and heterocyclic carbonyl compounds

| Example No. | Heterocyclic carbonyl compound | Catalyst conc. (m.moles) | Olefin conc. (m.moles) | DAE conc. (m.moles) | Solvent | Temp (°C.) | Yield of cyclopropane derivative (%) a | cis: trans | cis-1R,3S | cis-1S,3R | trans-1R,3R | trans-1S,3R |
|---|---|---|---|---|---|---|---|---|---|---|---|---|
| c | (Cu bronze) | 1.6 | 45 | 46 | DCE | 110 | 38 | 54:46 | 27 | 27 | 23 | 23 |
| c | d | 0.08 | 20 | 3.5 | PhMe/DCE | 85 | 11 | 56:44 | —b | —b | —b | —b |
| 15 | e | 0.1 | 16 | 3.5 | PhMe/DCE | 70 | — | 66:34 | 46 | 20 | 15 | 19 |
| 16 | f | 0.05 | 10 | 2.0 | PhMe | 80 | 3 | 55:45 | —b | —b | 27 | 18 | a Yield based on percentage decomposition of ethyl diazoacetate
b Estimation of populations not possible because of the occurrence of impurities which obscure the g.l.c. traces
c Comparative example
d Salicylaldehyde
e 2-Pyridinecarboxaldehyde:chloride
f 2-Pyrrolicarboxaldehyde

We claim:

1. A chiral Schiff base according to the general formula:

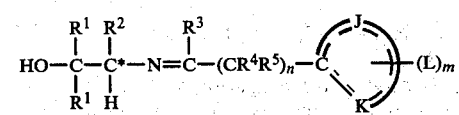

wherein $C^*$ is an asymmetric carbon atom, $R^1$ and $R^2$, which may be the same or different, are alkyl, aralkyl, aryl or alkaryl, $R^3$ is hydrogen, alkyl, aralkyl, aryl or alkaryl, $R^4$ and $R^5$, which may be the same or different, are hydrogen or lower alkyl, or where n is 1, $CR^4R^5$ may constitute a chain of 4 carbon atoms to n form a fused bicyclic ring system with the ring

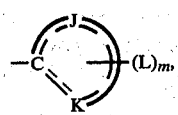

J is a chain of 3 or 4 atoms chosen from the group consisting of —C=C—C=C—, —C=N—C=C—, —C=C—N=C—, —N=C—C=C—, —S—C=C—, —O—C=C—, —NH—C=C—, =C—C=C— and =C—N=C—, which chain with the group C    K forms a substantially planar cyclic conjugated system containing $(4z+2)\pi$ electrons where z is a positive integer, K is nitrogen,

or —NH—, each L, which may be the same or different, represents a substituent attached to a carbon atom in the chain J and is selected from the group consisting of hydrogen, alkyl, aralkyl, alkaryl, aryl, hydroxy, $OR^6$, $OCOR^6$, CHO, $COR^6$, $CO_2H$, $CO_2R^6$, CN, $CONH_2$, $NH_2$, $NHR^6$, $NR_2^6$, $NHCOR^6$, $NO_2$, SH, $SR^6$, $SOR^6$, $SO_3H$, $SO_3R^6$ and a halogen atom, where $R^6$ is alkyl, aralkyl or aryl, with the proviso that where n is 0, the L's on two adjacent atoms in the chain J may constitute a chain of 4 carbon atoms to form, together with the ring

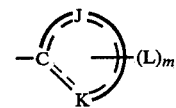

a fused bicyclic ring system, n is 0, 1 or 2, and m is equivalent to the number of carbon atoms in the chain J.

2. A chiral Schiff base as claimed in claim 1 wherein $R^1$ and $R^2$ are substituted phenyl groups, $R^3$ is hydrogen, n is 0 and the cyclic ring represents a pyridine, quinoline or pyrrole nucleus.

3. A chiral Schiff base as claimed in claim 2 wherein $R^1$ is a phenyl group having a substituent at least at the 2 position.

4. A chiral Schiff base as claimed in claim 1 wherein the asymmetric carbon atom has the R or S configuration.

5. A chiral Schiff base as claimed in claim 1 derivable from a S-2-amino-1,1-(2-alkoxyphenyl)-3-phenyl-1-propanol and a pyridinecarboxaldehyde, quinoline-carboxaldehyde or pyrrolecarboxaldehyde.

6. A metal complex which comprises a metal from the first or second series of the main group of transition metals in co-ordination with a chiral Schiff base as claimed in claim 5.

7. A metal complex as claimed in claim 6 in which the transition metal is selected from the group consisting of copper (II), chromium (II), manganese (II), iron (II), cobalt (II), nickel (II), and palladium (II).

8. A metal complex as claimed in claim 7 in which the transition metal is copper (II).

9. A metal complex as claimed in claim 6 which has the general structure

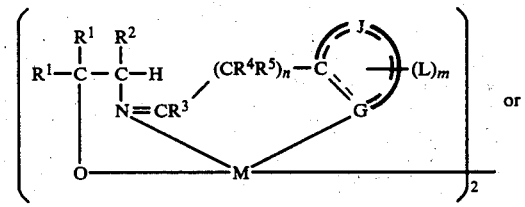

or

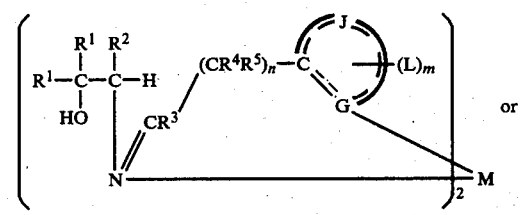

-continued

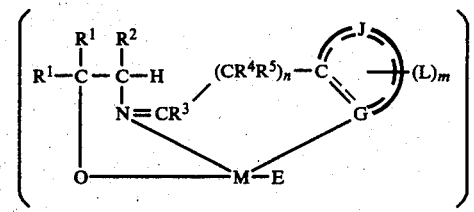

wherein $R^1$, $R^2$, $R^3$, $R^4$, $R^5$, J, L, m and n have the meanings previously ascribed to them, E is a monodentate neutral ligand, M is a metal from the first or second series of the main group of transition metals, and G is =N—,

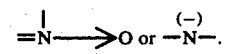

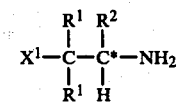

10. A process for preparing a Schiff base as claimed in claim 1 which process comprises reacting an amino alcohol of formula

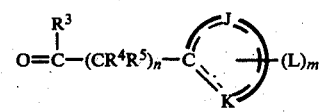

wherein at least C* is an asymmetric carbon atom, $X^1$ is a hydroxyl or protected hydroxyl group, and $R^1$ and $R^2$ are as defined in claim 1, with a heterocyclic carbonyl compound of formula wherein $R^3$, $R^4$, $R^5$, J, K, L, m and n are as defined in claim 1.

11. A process for preparing a chiral transition metal complex which process comprises reacting a chiral Schiff base as claimed in claim 1 with a transition metal salt of an inorganic acid.

12. A process for preparing a chiral transition metal complex as claimed in claim 6 which comprises reacting a suitable primary amine in which the amino group is bonded to a chiral carbon atom with a suitable transition metal complex.

13. A process for preparing a chiral transition metal complex which comprises reacting a chiral Schiff base as claimed in claim 1 with a suitable transition metal complex.

14. A process for preparing a chiral transition metal complex which comprises reacting a chiral Schiff base as claimed in claim 1 with a suitable transition metal carboxylate.

* * * * *